(12) United States Patent
Potyrailo et al.

(10) Patent No.: US 7,775,083 B2
(45) Date of Patent: Aug. 17, 2010

(54) SYSTEM AND METHOD FOR MONITORING PARAMETERS IN CONTAINERS

(75) Inventors: Radislav A. Potyrailo, Niskayuna, NY (US); Vincent F. Pizzi, Millis, MA (US); Hua Wang, Clifton Park, NY (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 579 days.

(21) Appl. No.: 11/536,030

(22) Filed: Sep. 28, 2006

(65) Prior Publication Data
US 2008/0012577 A1 Jan. 17, 2008

Related U.S. Application Data

(60) Provisional application No. 60/803,265, filed on May 26, 2006.

(51) Int. Cl.
*G01N 22/00* (2006.01)
*G01R 27/04* (2006.01)

(52) U.S. Cl. .................................. 73/19.01; 73/53.01

(58) Field of Classification Search ............... 73/19.01, 73/53.01; 340/10.41
See application file for complete search history.

(56) References Cited

U.S. PATENT DOCUMENTS

| | | |
|---|---|---|
| 5,497,140 A | 3/1996 | Tuttle |
| 5,514,337 A | 5/1996 | Groger et al. |
| 5,597,534 A | 1/1997 | Kaiser |
| 5,646,592 A | 7/1997 | Tuttle |
| 5,785,181 A | 7/1998 | Quartararo, Jr. et al. |
| 5,892,458 A | 4/1999 | Anderer et al. |
| 6,025,725 A | 2/2000 | Gershenfeld et al. |
| 6,053,031 A | 4/2000 | Kullik et al. |
| 6,054,935 A | 4/2000 | Urbas et al. |
| 6,147,606 A | 11/2000 | Duan |
| 6,204,764 B1 | 3/2001 | Maloney |
| 6,278,379 B1 | 8/2001 | Allen et al. |
| 6,359,444 B1 | 3/2002 | Grimes |
| 6,369,712 B2 | 4/2002 | Letkomiller et al. |
| 6,586,946 B2 | 7/2003 | Hefti et al. |

(Continued)

FOREIGN PATENT DOCUMENTS

WO WO2005/074161 8/2005

OTHER PUBLICATIONS

Want, R., "Enabling Ubiquitous Sensing with RFID", Computer, Apr. 2004, pp. 84-86.

(Continued)

*Primary Examiner*—Daniel S Larkin
(74) *Attorney, Agent, or Firm*—Yonggang Ji

(57) ABSTRACT

A system for measuring parameters in a container is disclosed. A system for measuring multiple parameters includes a container having a solution, at least one sensor in conjunction with a tag is in proximity to an impedance analyzer and a reader that constitute a measurement device. The at least one sensor is configured to determine at least one parameter of the solution. The tag is configured to provide a digital ID associated with the sensor, where the container is in proximity to the reader and an impedance analyzer. The impedance analyzer is configured to send and receive a given range of frequencies from the sensor, based on the parameter and calculate parameter changes based on the response.

30 Claims, 14 Drawing Sheets

U.S. PATENT DOCUMENTS

| | | |
|---|---|---|
| 6,639,402 B2 | 10/2003 | Grimes et al. |
| 6,672,512 B2 | 1/2004 | Bridgelall |
| 6,724,310 B1 | 4/2004 | Gershenfeld et al. |
| 6,824,521 B2 | 11/2004 | Rich et al. |
| 7,015,826 B1 | 3/2006 | Chan et al. |
| 7,021,132 B2 | 4/2006 | Nigon et al. |
| 7,038,470 B1 | 5/2006 | Johnson |
| 7,050,017 B2 | 5/2006 | King et al. |
| 2001/0045899 A1 | 11/2001 | Hoek |
| 2003/0117321 A1 | 6/2003 | Furse et al. |
| 2004/0113790 A1 | 6/2004 | Hamel et al. |
| 2005/0156207 A1 | 7/2005 | Yazawa et al. |
| 2005/0192488 A1 | 9/2005 | Bryenton et al. |
| 2006/0210440 A1* | 9/2006 | Potyrailo et al. ......... 422/82.01 |

OTHER PUBLICATIONS

Rusko, M., et al., "Passive Resonator Identification Tag for Narrow-Band Wireless Telemetry", IEEE Ultrasonics Symposium, 1999, pp. 377-380.

Jurs, P. C., et al., "Computational Methods for the Analysis of Chemical Sensor Array Data from Volatile Analytes", Chemical Reviews, 2000, vol. 100, pp. 2649-2678.

* cited by examiner

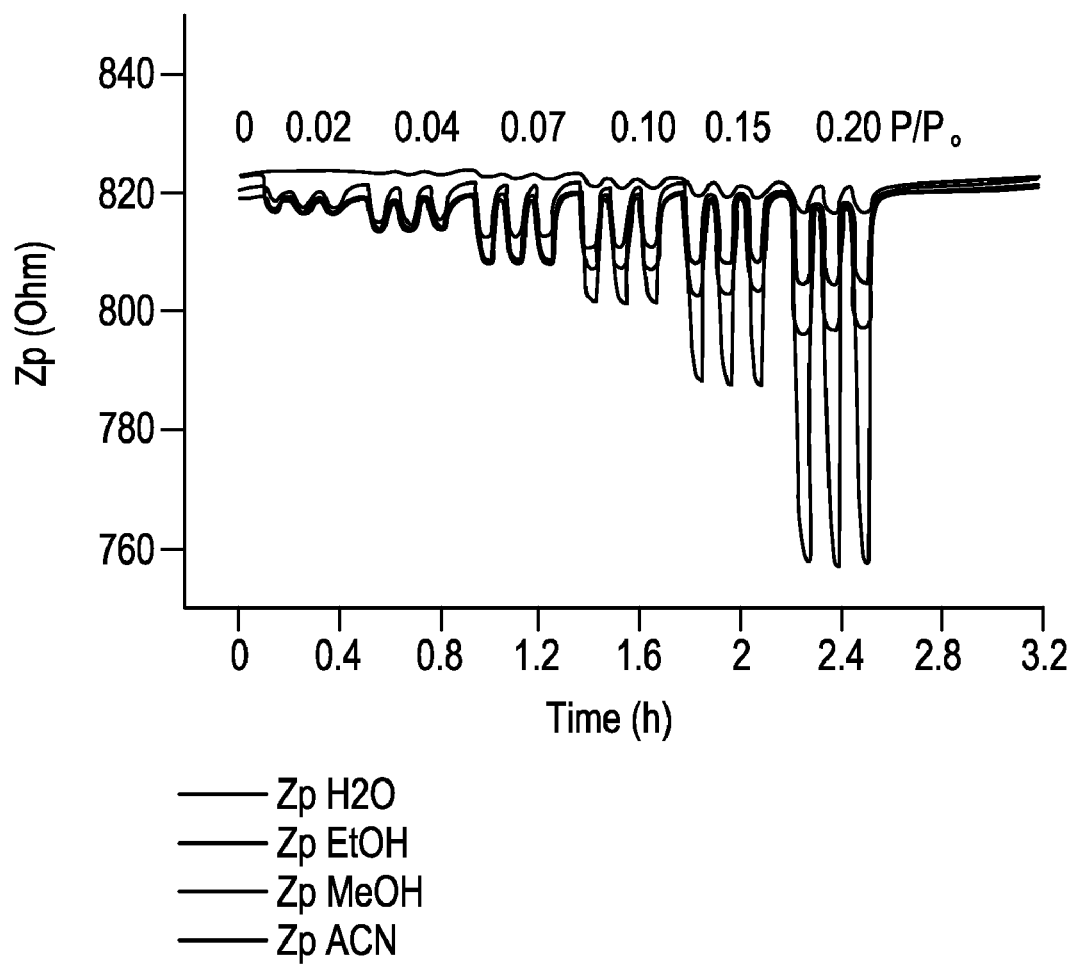

SYSTEM AND METHOD FOR MONITORING PARAMETERS IN CONTAINERS

CROSS-REFERENCE TO RELATED APPLICATIONS

This application claims priority to U.S. provisional patent application No. 60/803,265 filed May 26, 2006; the disclosure of which is incorporated herein by reference in its entirety.

FIELD OF THE INVENTION

This invention relates to a system for monitoring parameters in containers.

BACKGROUND OF THE INVENTION

In order to keep humans safe from solutions, such as liquids, gases and solids that may be toxic or harmful to them different devices are used to test the solutions to determine if they are harmful. These devices include chemical or biological sensors that attach an identification marker with an antibody. For example, some chemical/biological sensors include a chip attached to an antibody, where the chip includes a fluorescent marker identifying the specific anybody.

There are known chemical or biological sensors that include structural elements that are formed from a material that selectively responds to a specific analyte as shown in U.S. Pat. No. 6,359,444. Other known chemical or biological sensors include an electromagnetically active material that is located in a specific position on the sensors that may be altered by an external condition as indicated in U.S. Pat. No. 6,025,725. Some known chemical or biological sensor systems include components for measuring more than one electrical parameters as shown in U.S. Pat. No. 6,586,946.

The aforementioned sensors do not address the need to maintain a sterile barrier between the person, the sensor and the solution while the material in the solution is tested to determine what chemical or biological material is in the solution. By maintaining a sterile barrier there is a lower risk of contamination for a human that is in contact with the solution. Conversely, the contents of the container, if sterile, are not at risk of adventitious contamination. Also, the above-mentioned sensors do not allow one to test for various chemical, physical and biological parameters in the solution as needed. Therefore, there is a need for a system that enables a user to simply test for chemical and/or biological material in a solution non-invasively, while the solution is in a sterile barrier where the user can safely obtain measurements for the material.

BRIEF SUMMARY OF THE INVENTION

The present invention has been accomplished in view of the above-mentioned technical background, and it is an object of the present invention to provide a system and method for monitoring parameters in a biological container.

In a preferred embodiment of the invention, a system for measuring parameters in a container is disclosed. A system for measuring multiple parameters includes a container having a solution, at least one sensor in conjunction with a tag is in proximity to an impedance analyzer and a reader that constitute a measurement device. The at least one sensor is configured to determine at least one parameter of the solution. The tag is configured to provide a digital ID associated with the sensor, where the container is in proximity to the reader and an impedance analyzer. The impedance analyzer is configured to send and receive a given range of frequencies from the sensor, based on the parameter and calculate parameter changes based on the response.

In another preferred embodiment of the invention, an apparatus for measuring a parameter in a container is disclosed. There is a container having a solution, at least one sensor in conjunction with a tag in proximity to a measurement device. The at least one sensor is configured to determine at least one parameter of the solution. The measurement device is configured to read the at least one parameter from the at least one sensor.

BRIEF DESCRIPTION OF THE DRAWINGS

These and other advantages of the present invention will become more apparent as the following description is read in conjunction with the accompanying drawings, wherein:

FIG. 9 is a graphical representation of an example of a Zp response of FIG. 4 in accordance with the invention.

DETAILED DESCRIPTION OF THE INVENTION

The presently preferred embodiments of the invention are described with reference to the drawings, where like components are identified with the same numerals. The descriptions of the preferred embodiments are exemplary and are not intended to limit the scope of the invention.

Figure 1:
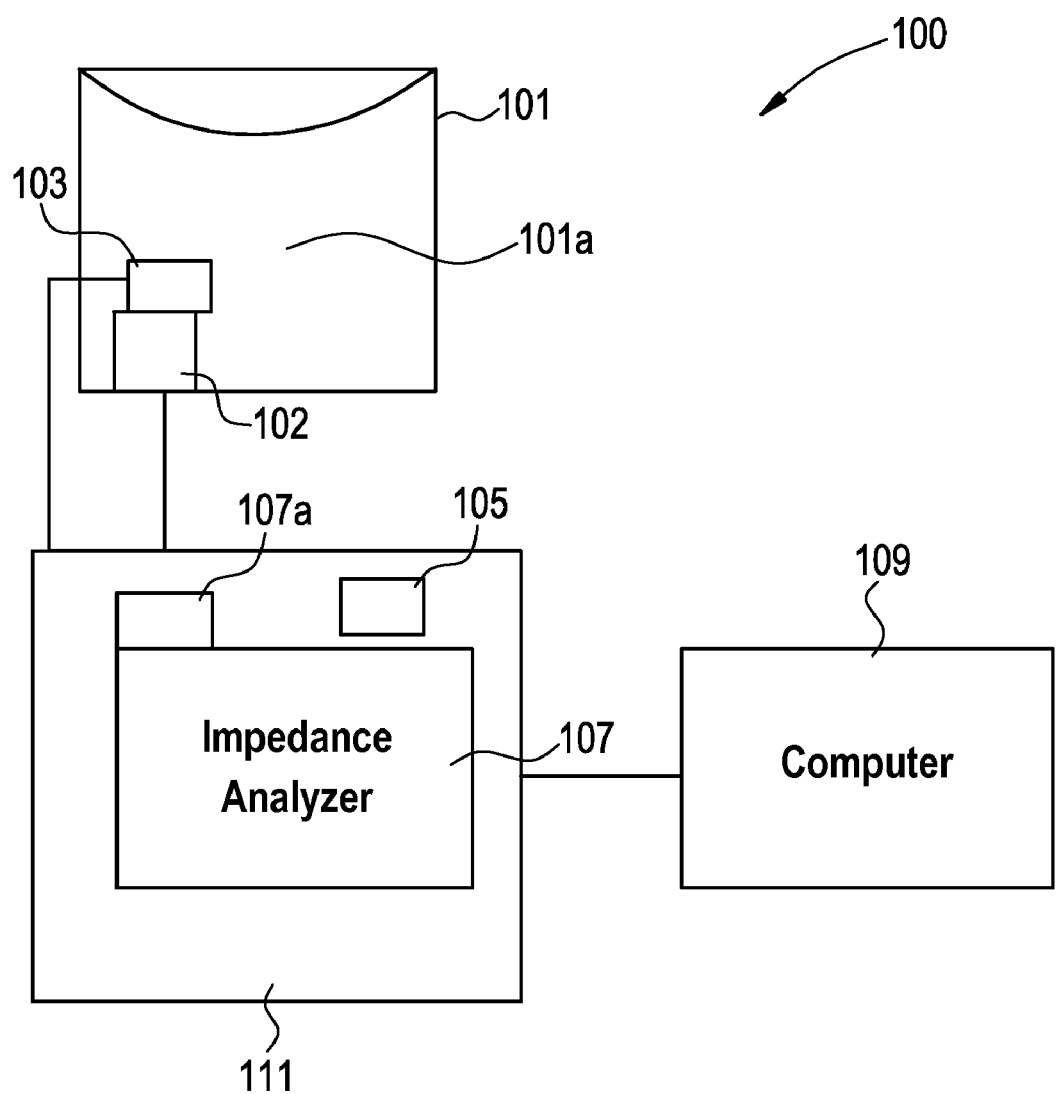
FIG. 1 illustrates a block diagram of a system for monitoring parameters in a container in accordance with an embodiment of the invention.

FIG. 1 illustrates a block diagram of a system for monitoring parameters of a solution in a container. The system 100 includes a container 101, a tag 102 and a sensor 103 on the tag 102, a reader 105, an impedance analyzer 107, a standard computer 109 and a measurement device 111. Measurement device 111 is made of the reader 105 and the impedance analyzer 107. Several sensors 103 may be formed on the tag 102 in an array format. The sensor 103 or sensor array 103 is located in container 101, which is connected by a wireless connection or an electrical wire connection to the impedance analyzer 107 and the computer 109. The sensor 103, the tag 102 or the sensor array 103 are connected by a wireless connect or an electrical wire to the measurement device 111 and the computer 109. Impedance analyzer 107 is connected by a wireless connection or an electrical wire connection to the computer 109. Container 101 may be a disposable container, a stainless steel container, a plastic container, a polymeric material container, a pre-sterilized polymeric material container or any type of container known to those of ordinary skill in the art that can hold a solution 101a. Inside the container 101 is the solution 101a, the solution 101a may be a liquid, fluid or gas, a solid, a paste or a combination of liquid and solid. For example, the solution 101a may be blood, water, a biological buffer or gas. The solution 101a may contain toxic industrial material, chemical warfare agent, gas, vapors or explosives disease marker in exhaled breath, bio-pathogen in water, virus, bacteria and other pathogens. If the solution 101a is blood it may contain various materials such as creatinine, urea, lactate dehydrognease, alkaline phosphate, potassium, total protein, sodium, uric acid, dissolved gases and vapors, such as $CO_2$, $O_2$, NOx, ethanol, methanol, halothane, benzene, chloroform, toluene, chemical warfare agents, vapor or explosives and the like. On the other hand if the solution 101a is a gas or vapor, it may be $CO_2$, $O_2$, NOx, ethanol, methanol, halothane, benzene, chloroform toluene or chemical warfare agent. If the solution 101a is a toxic industrial agent that can be inhaled and dissolved in blood then in may be Ammonia, Acetone cyanohydrin, Arsenic tricholoride, Chlorine, carbonyl sulfide or the like. In the case where the solution 101a is a chemical war agent it may be Tabun, Sarin, Soman, Vx, blister agents, Mustard gas, choking agent or a blood agent. If the solution 101a is a disease marker in exhaled breath it may be acetaldehyde, Acetone, carbon monoxide and the like. If the solution 101a includes a bio-pathogen then it may be anthrax, brucellosis, shigella, tularemia or the like. Further, the solution 101a in the container may include prokaryotic and eukaryotic cells to express proteins, recombinant proteins, virus, plasmids, vaccines, bacteria, virus, living tissue and the like. Container 101 can be of different size, for example, a single biological cell, micro fluidic channel, a micro titer plate, a Petri dish, a glove box, a hood, a walk-in hood, a room in a building, a building. Thus, container can be of any size where sensor and tag are positioned to measure environment in the container. Sensor and tag can be stationary in the container or attached to some parts inside the container, where parts are moving as a function of time. Examples of parts are individual viruses, individual cells, home pets, people, etc.

In close proximity to the solution 101a or in the solution 101a is the plurality of sensors in the array 103. Reader 105 is located in the measurement device 111 outside of the container 101. An antenna 301 (FIG. 3) of tag 102 when covered by a polymer inorganic, composite or other type of film nanofiber mesh or nanostructured coating is the sensor 103 or the sensor array 103. A plurality of sensors in an array 103 can be a typical sensor or typical sensor array known to those of ordinary skill in the art or the plurality of sensors in an array may be radio frequency identification (RFID) sensors array 103. RFID sensors in the array 103 are devices that are responsible for creating a useful signal based on a parameter from the solution 101a. The parameters include conductivity measurement, pH level, temperature, blood relevant measurement, ionic measurement, non ionic measurement, non-conductivity, electromagnetic radiation level measurement and pressure. The plurality of sensors in the array 103 are covered or wrapped in a typical sensor film that enables it to obtain parameters of the solution 101a. Each sensor is associated with same or different sensing film. The typical sensor film is a polymer, organic, inorganic, biological, composite, or nanocomposite film that changes its electrical property based on the solution 101a that it is placed in. The sensor film may be a hydrogel such as (poly-(2-hydroxyethy) methacrylate, a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-hydrogel film, electrospun polymer nanofibers, metal nanoparticle hydrogen film electrospun inorganic nanofibers, electrospun composite nanofibers, and any other sensor material. In order to prevent the material in the sensor film from leaking into the container 101, the sensor materials are attached to the surface of the plurality of sensors array 103 using the standard techniques, such as covalent bonding, electrostatic bonding and other standard techniques known to those of ordinary skill in the art. Each of the plurality of RFID sensors in the array 103 may measure the parameter individually or each sensor 103 may measure all of the parameters. For example, a sensor array of RFID sensor array 103 may only measure temperature of solution 101a or the sensor array of the plurality of RFID sensor array 103 may measure the conductivity, the pH and the temperature of the solution 101a. In addition, the plurality of RFID sensors in the array 103 are transponders that include a receiver to receive signals and a transmitter to transmit signals. The sensor 103 may act as a typical RFID sensor that is passive, semi-active or active.

Figure 3:
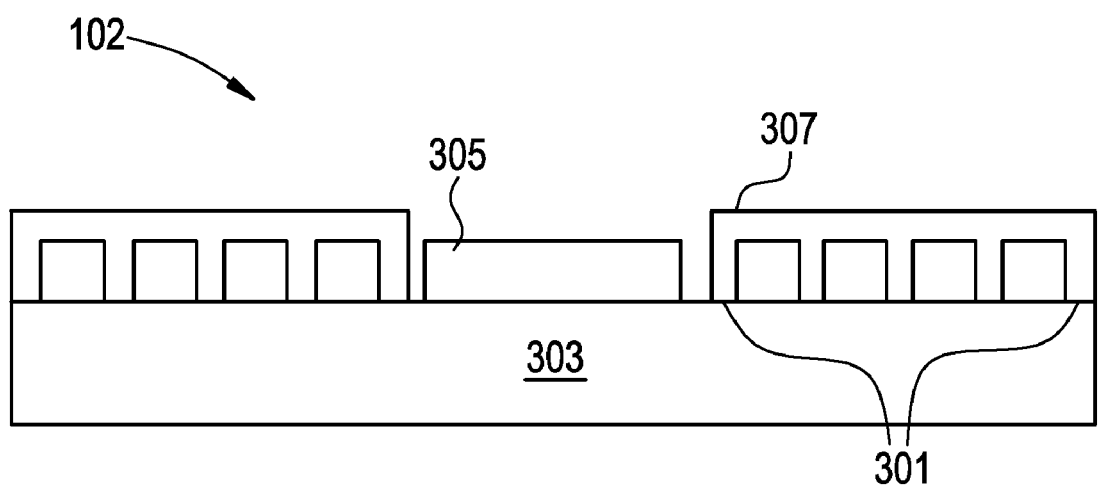
FIG. 3 illustrates an exploded view of the radio frequency identification (RFID) tag of FIG. 1 in accordance with the invention.

FIG. 3 illustrates a radio frequency identification (RFID) tag. The RFID tag 102 may also be referred to as a wireless sensor. RFID tag 102 includes a chip or substrate 303 upon which is disposed an antenna 301 and a capacitor 305. A wide variety of commercially available tags can be applied for the deposition of sensor structures. These tags operate at different frequencies ranging from about 125 kHz to about 2.4 GHz. Suitable tags are available from different suppliers and distributors, such as Texas Instruments, TagSys, Digi Key, Amtel, Hitachi and others. Suitable tags can operate in passive, semi-passive and active modes. The passive RFID tag does not need a power source for operation, while the semi-passive and active RFID tags rely on the use of onboard power for their operation. RFID tag 102 has a digital ID and the frequency response of the antenna circuit of the RFID tag 102 can be measured as the complex impedance with real and imaginary parts of the complex impedance. Also, the RFID tag 102 may be a transponder, which is an automatic device that receives, amplifies and retransmits a signal on a different frequency. Further, the RFID tag 102 may be another type of transponder that transmits a predetermined message in response to a predefined received signal. This RFID tag 102 is equivalent to the variety of RFID tags disclosed in "Modified RF Tags and their Applications for Multiplexed Detection" filed on Oct. 26, 2005, and assigned U.S. patent application Ser. No. 11/259,710 and "Multivariates Methods of Chemical and Biological Detection Using Radio-Frequency Identification Tags" filed on Oct. 26, 2005, and assigned U.S. patent application Ser. No. 11/259,711, the disclosures of which are hereby incorporated by reference in their entireties.

Antenna 301 is an integrated part of the sensor 103. A plurality of RFID sensors 130 are located at approximately at a distance of 1-100 cm from the reader 105 and impedance analyzer 107. In another embodiment of the invention, the RFID antenna 301 includes chemical or biological sensitive materials 307 used as part of the antenna material to modulate antenna properties. These chemical and biological materials are conductive sensitive materials such as inorganic, polymeric, composite sensor materials and the like. The composite sensor materials include a base material that is blended with conductive soluble or insoluble additive. This additive is in the form of particles, fibers, flakes, and other forms that provide electrical conductance. In yet another embodiment of the invention, the RFID antenna 301 includes chemical or biological sensitive materials used as part of the antenna material to modulate antenna electrical properties. The chemical or biological sensitive materials are deposited on the RFID antenna 301 by arraying, ink jet printing, screen printing, vapor deposition, spraying, draw coating, and other typical depositions known to those of ordinary skill in the art. In yet another embodiment of the invention, where the temperature of solution 101$a$ (FIG. 1) is being measured the chemical or biological material covering the antenna 301 may be a material that is selected to shrink or swell upon temperature changes. This type of sensor material may contain an additive that is electrically conductive. The additive may be in the form of micro particles or nano-particles, for example carbon black powder, or carbon nano-tubes or metal nano-particles. When the temperature of the sensor film 307 changes these individual particles of the additive changes, which affects the overall electrical conductivity in the sensor film 307.

In addition to coating the sensor 103 with the sensing film 307, some physical parameters such as temperature, pressure, conductivity of solution, and others are measured without coating the sensor 103 with the sensing film 307. These measurements rely on the changes of the antenna properties as a function of physical parameter without having a special sensing film applied onto the sensor 103.

Figure 2A:
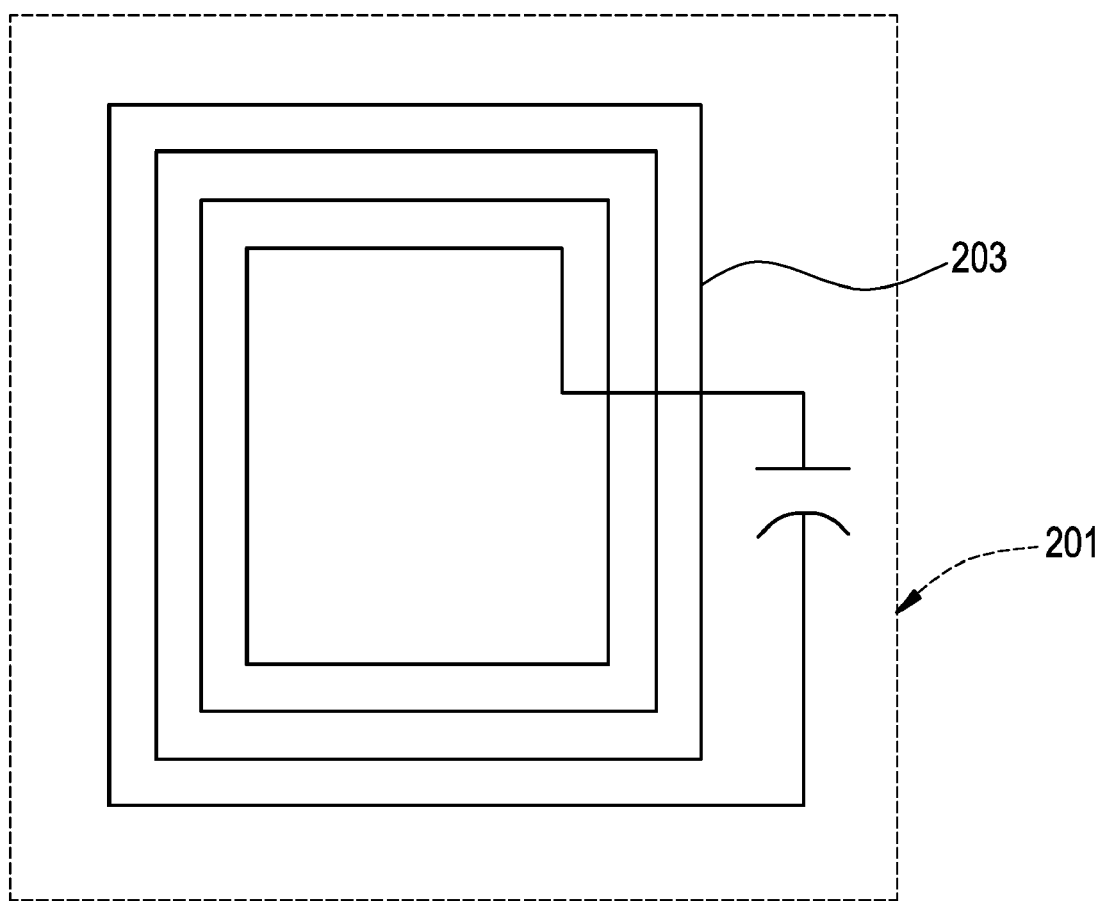
FIGS. 2A, 2B, 2C and 2D are schematic diagrams of circuitry for RFID systems constructed in accordance with the invention.

While several embodiments of wireless sensors 102 are illustrated, it should be appreciated that other embodiments are within the scope of the invention. For example, circuitry contained on the wireless sensor may utilize power from the illuminating RF energy to drive a high Q resonant circuit, such as the circuit 203 within the capacitance based sensor 201 illustrated in FIG. 2A. The high Q resonant circuit 203 has a frequency of oscillation determined by the sensor 201 or sensor 102 incorporates a capacitor whose capacitance varies with the sensed quantity. The illuminating RF energy may be varied in frequency, and the reflected energy of the sensor is observed. Upon maximizing the reflect energy, a resonant frequency of the circuit 203 is determined. The resonant frequency may then be converted into a parameter, discussed above, of the sensor 201 or 102.

Figure 2B:
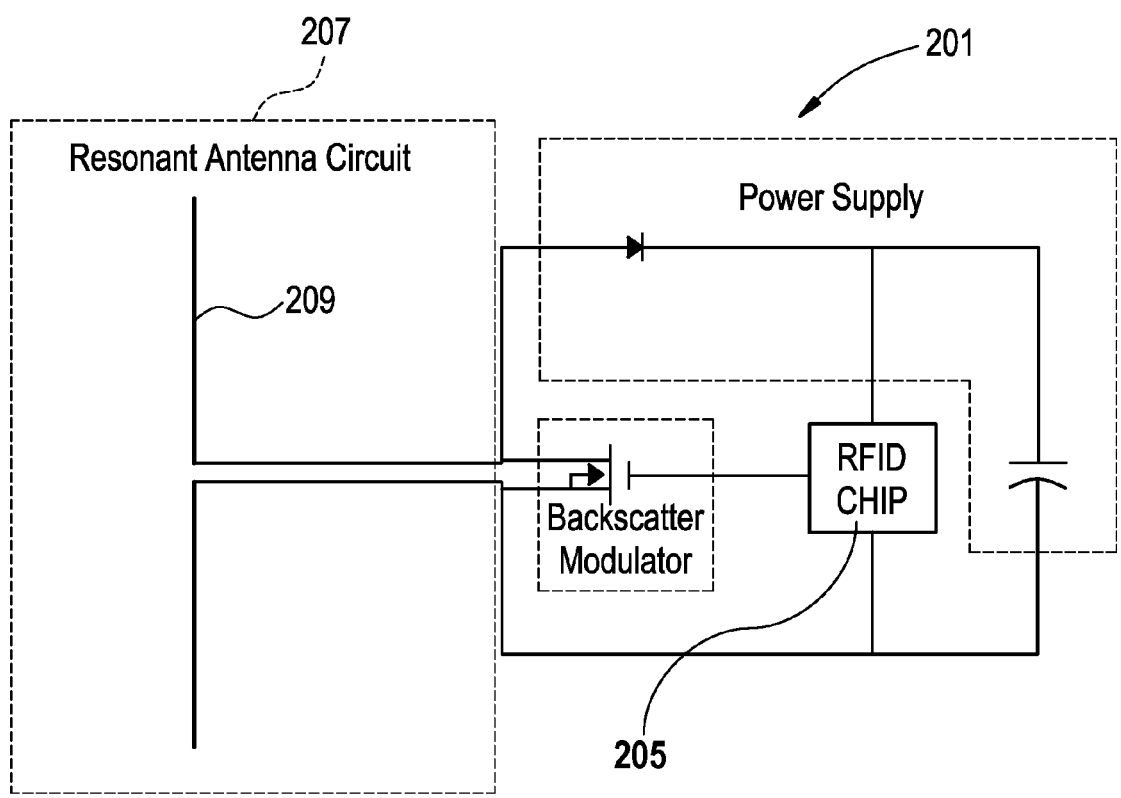
Figure 2C:
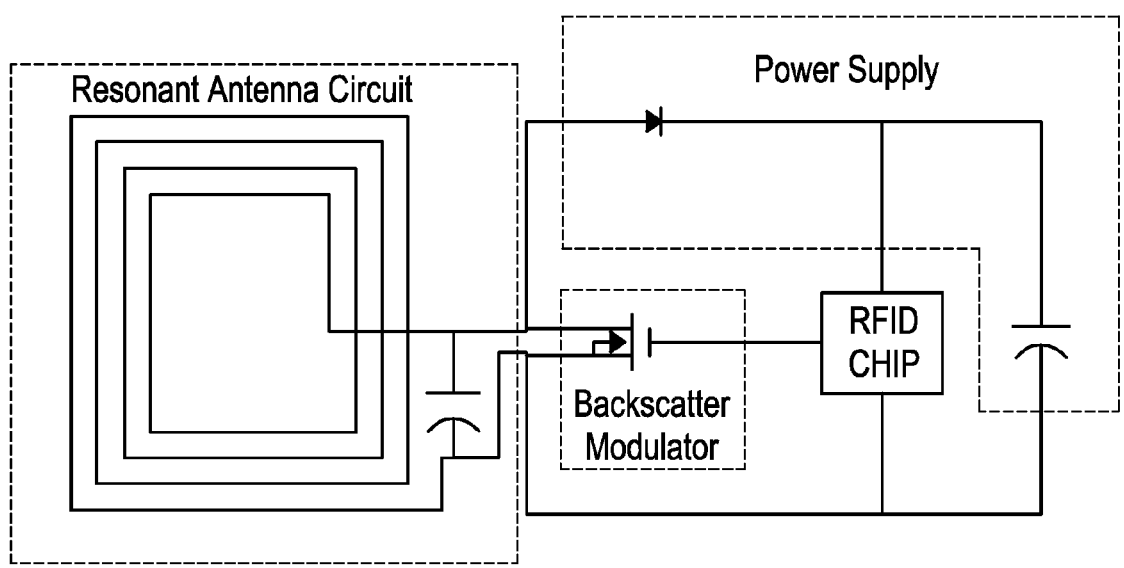
Figure 2D:
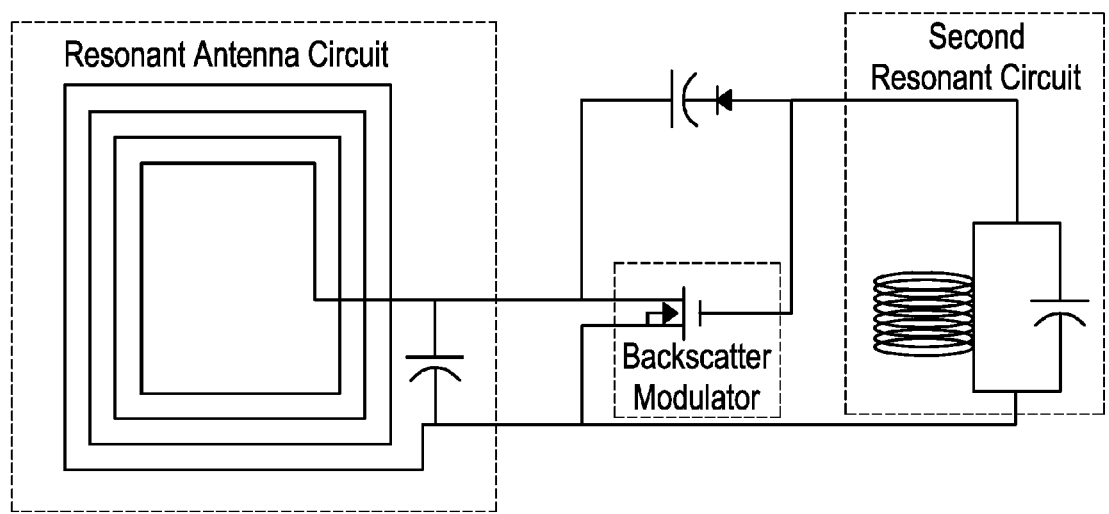

In other embodiments, illuminating RF energy is pulsed at a certain repetitive frequency close to the resonant frequency of a high Q oscillator. For example, as illustrated in FIG. 2B, the pulsed energy is rectified in a wireless sensor 205 or 102 (FIG. 1) and is used to drive a high Q resonant circuit 207 having a resonant frequency of oscillation determined by the sensor 205 to which it is connected. After a period of time, the pulsed RF energy is stopped and a steady level of illuminating RF energy is transmitted. The high Q resonant circuit 207 is used to modulate the impedance of the antenna 209 using the energy stored in the high Q resonant circuit 207. A reflected RF signal is received and examined for sidebands. The frequency difference between the sidebands and the illuminating frequency is the resonant frequency of the circuit 201. FIG. 2C illustrates another embodiment of wireless sensors used for driving high Q resonant circuits. FIG. 2D illustrates a wireless sensor that may include both a resonant antenna circuit and a sensor resonant circuit, which may include an LC tank circuit. The resonant frequency of the antenna circuit is a higher frequency than the resonant frequency of the sensor circuit, for example, as much as four to 1000 times higher. The sensor circuit has a resonant frequency that may vary with some sensed environmental condition. The two resonant circuits may be connected in such a way that when alternating current (AC) energy is received by the antenna resonant circuit, it applies direct current energy to the sensor resonant circuit. The AC energy may be supplied through the use of a diode and a capacitor, and the AC energy may be transmitted to the sensor resonant circuit through the LC tank circuit through either a tap within the L of the LC tank circuit or a tap within the C of the LC tank circuit. Further, the two resonant circuits may be connected such that voltage from the sensor resonant circuit may change the impedance of the antenna resonant circuit. The modulation of the impedance of the antenna circuit may be accomplished through the use of a transistor, for example a FET.

Alternatively, illuminating radio frequency (RF) energy is pulsed at a certain repetitive frequency. The pulsed energy is rectified in a wireless sensor (FIGS. 2A-2D) and is used to drive a high Q resonant circuit having a resonant frequency of oscillation determined by the sensor to which it is connected. After a period of time, the pulsed RF energy is stopped and a steady level of illuminating RF energy is transmitted.

The resonant circuit is used to modulate the impedance of the antenna using the energy stored in the high Q resonant circuit. A reflected RF signal is received and examined for sidebands. The process is repeated for multiple different pulse repetition frequencies. The pulse repetition frequency that maximizes the amplitude of the sidebands of the returned signal is determined to be the resonant frequency of the resonant circuit. The resonant frequency is then converted into a parameter or measurement on the resonant circuit.

Referring to FIG. 1, below the RFID tag 102 is the RFID reader 105 and impedance analyzer 107 (measurement device 111) which provides information about real and complex impedance of the RFID tag 102 based on reading the information from the RFID antenna 301. Also, the reader 105 reads the digital ID from the RFID tag 102. The reader 105 may also be referred to as a radio frequency identification (RFID) reader. RFID tag 102 is connected by a wireless connection or an electrical wire to the RFID reader 105 and the impedance analyzer 107. The RFID reader 105 and the impedance analyzer 107 (measurement device 111) are connected by a wireless or electrical wire connection to the standard computer 109. This system may operate in three ways that include: 1. the read system of the RFID reader 105, where the RFID reader 105 will read information from the plurality of RFID sensors in the array 103 to obtain chemical or biological information and the RFID reader 105 that reads the digital ID of the RFID tag 102; 2. the RFID reader 105 reads the digital ID of the RFID tag 102 and the impedance analyzer 107 reads the antenna 301 to obtain the complex impedance; and 3. if there are a plurality of RFID sensors 103 with and without sensor films where the RFID reader 105 will read information from the plurality of RFID sensors in the array 103 to obtain chemical or biological information and the RFID 105 reader reads the digital ID of the RFID tag 102 and the RFID reader 105 reads the digital ID of the RFID tag 102 and the impedance analyzer 107 reads the antenna 301 to obtain the complex impedance.

Measurement device 111 or computer 109 includes a pattern recognition subcomponent (not shown). Pattern recognition techniques are included in the pattern recognition subcomponent. These pattern recognition techniques on collected signals from each sensor 103 or the plurality of RFID sensors in the array 103 may be utilized to find similarities and differences between measured data points. This approach provides a technique for warning of the occurrence of abnormalities in the measured data. These techniques can reveal correlated patterns in large data sets, can determine the structural relationship among screening hits, and can significantly reduce data dimensionality to make it more manageable in the database. Methods of pattern recognition include principal component analysis (PCA), hierarchical cluster analysis (HCA), soft independent modeling of class analogies (SIMCA), neural networks and other methods of pattern recognition known to those of ordinary skill in the art. The distance between the reader 105 and the plurality of RFID sensors in the array 103 or sensor 103 is kept constant or can be variable. The impedance analyzer 107 or the measurement device 111 periodically measures the reflected radio frequency (RF) signal from the plurality of RFID sensors in the array 103. Periodic measurements from the same sensor 103 or the plurality of RFID sensors in the array 103 provide information about the rate of change of a sensor signal, which is related to the status of the chemical/biological/physical environment surrounding the plurality of RFID sensors in the array 103. In this embodiment, the measurement device 111 is able to read and quantify the intensity of the signal from the plurality of RFID sensors in the array 103.

In proximity of the RFID reader 105 is the impedance analyzer 107, which is an instrument used to analyze the frequency-dependent properties of electrical networks, especially those properties associated with reflection and transmission of electrical signals. Also, the impedance analyzer 107 may be a laboratory equipment or a portable specially made device that scans across a given range of frequencies to measure both real and imaginary parts of the complex impedance of the resonant antenna 301 circuit of the RFID tag 102. In addition, this impedance analyzer 107 includes database of frequencies for various materials associated with the solution 101a described above. Further, this impedance analyzer 107 can be a network analyzer (for example Hewlett Packard 8751A or Agilent E5062A) or a precision impedance analyzer (Agilent 4249A).

Computer 109 is a typical computer that includes: a processor, an input/output (I/O) controller, a mass storage, a memory, a video adapter, a connection interface and a system bus that operatively, electrically or wirelessly, couples the aforementioned systems components to the processor. Also, the system bus, electrically or wirelessly, operatively couples typical computer system components to the processor. The processor may be referred to as a processing unit, a central processing unit (CPU), a plurality of processing units or a parallel processing unit. System bus may be a typical bus associated with a conventional computer. Memory includes a read only memory (ROM) and a random access memory (RAM). ROM includes a typical input/output system including basic routines, which assists in transferring information between components of the computer during start-up.

Above the memory is the mass storage, which includes: 1. a hard disk drive component for reading from and writing to a hard disk and a hard disk drive interface, 2. a magnetic disk drive and a hard disk drive interface and 3. an optical disk drive for reading from or writing to a removable optical disk such as a CD-ROM or other optical media and an optical disk drive interface (not shown). The aforementioned drives and their associated computer readable media provide non-volatile storage of computer-readable instructions, data structures, program modules and other data for the computer 109.

Also, the aforementioned drives may include the algorithm, software or equation for obtaining the parameters for the solution 101a, which will be described in the flow charts of FIGS. 4, 5 and 6 that works with the processor of computer 109. In another embodiment, the obtaining parameters of the solution 101a algorithm, software or equation may be stored in the processor, memory or any other part of the computer 109 known to those of ordinary skill in the art.

Figure 4:
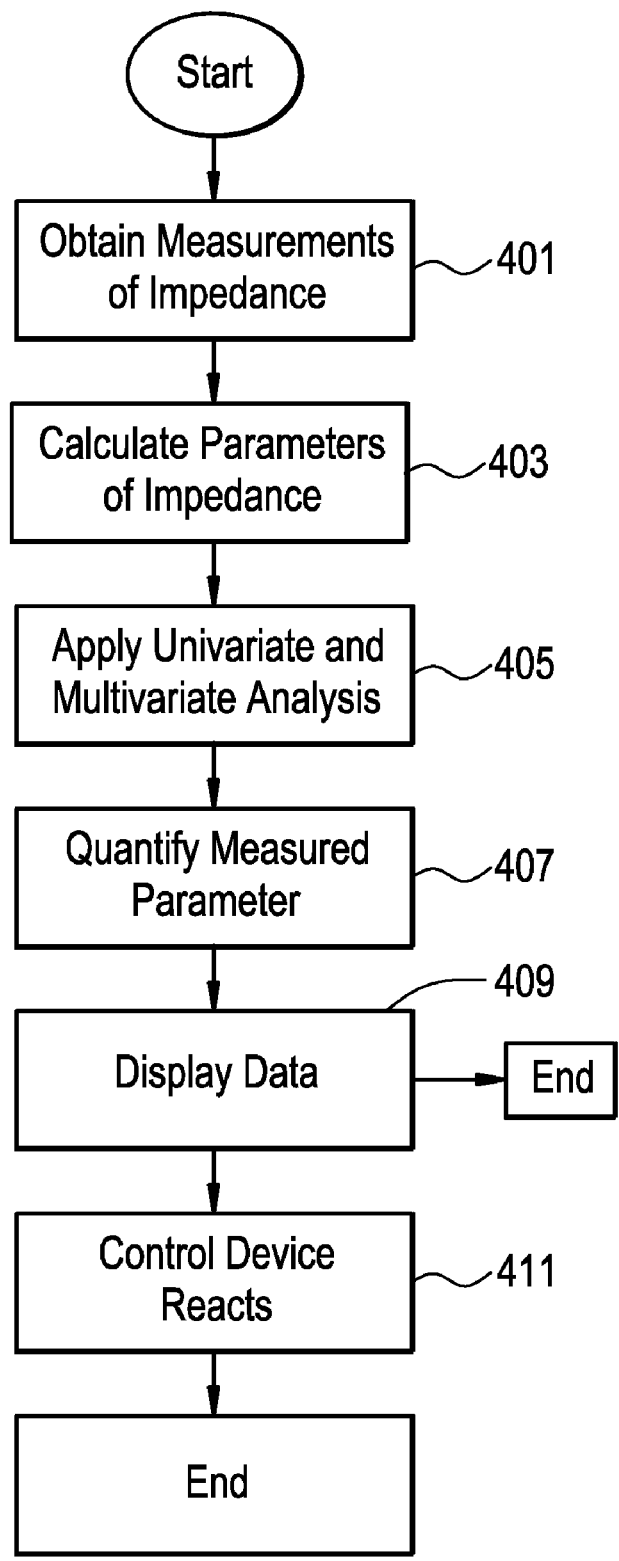
FIG. 4 depicts a flow chart of how the system for monitoring parameter in a solution is employed in accordance with the invention.

FIG. 4 is a flow chart that shows how the system for monitoring parameters in a solution is employed. This process starts from FIG. 1 where the container 101 has a sensor 103. The sensor 103 is read with an impedance analyzer 107 that is connected to the computer 109. As stated above, the impedance analyzer 107 is wirelessly or electrically connected (wired) to the plurality of RFID sensors in the array 103 at block 401, the impedance analyzer 107 measures complex impedance Z from the plurality of RFID sensors in the array 103 as a function of frequency over a chosen frequency range with a predetermined frequency resolution with a predetermined acquisition speed. Other non-limiting parameters that can be preset for measurements can include number of averages, smoothing etc. Impedance analyzer 107 includes a pickup antenna 107a (FIG. 1) which excites the plurality of RFID sensors in the array 103 and the pickup antenna collects a reflected radio frequency signal from the plurality of RFID sensors in the arrays 103. The plurality of RFID sensors in the array 103 are able to obtain the parameters, such as conductivity, temperature, pH and other parameters disclosed above based on the polymer or sensor film 307 or without the sensor film 307 that detects these parameters in the solution 101a.

Figure 7:
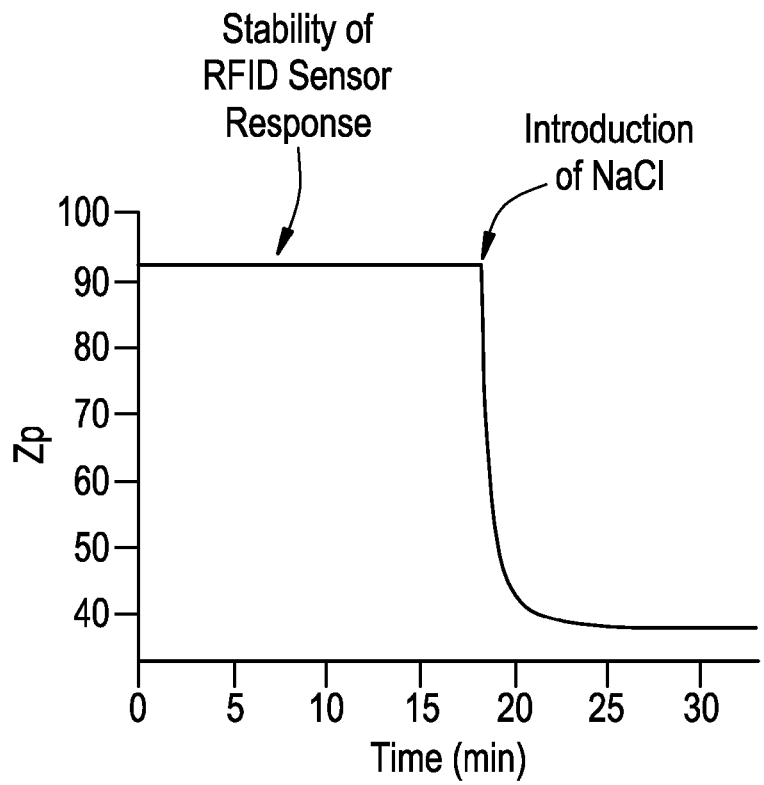
FIG. 7 is another graphical representation of an example of the utilization of the system for monitoring parameters in a solution of FIG. 1. in accordance with the invention.
Figure 8:
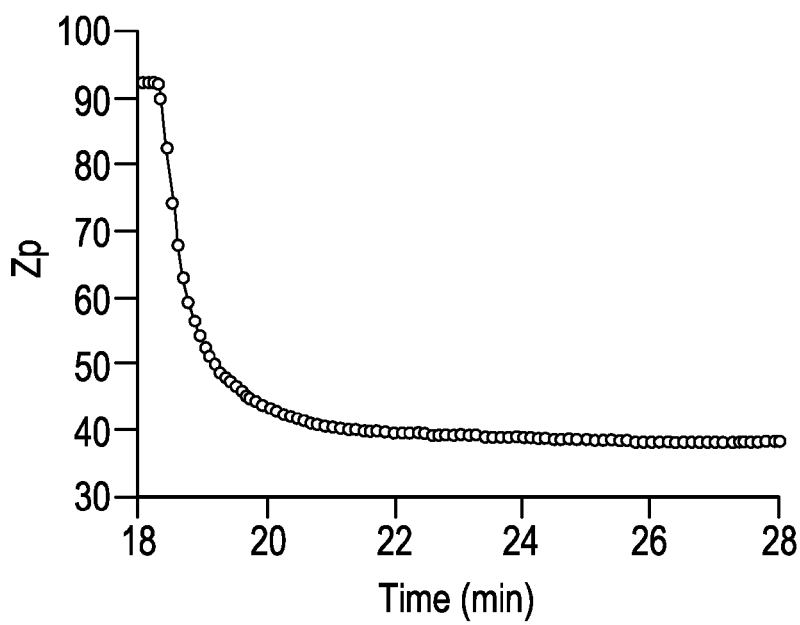
FIG. 8 is yet another graphical representation of an example of the utilization of the system for monitoring parameters in a solution of FIG. 1. in accordance with the invention.
Figure 10A:
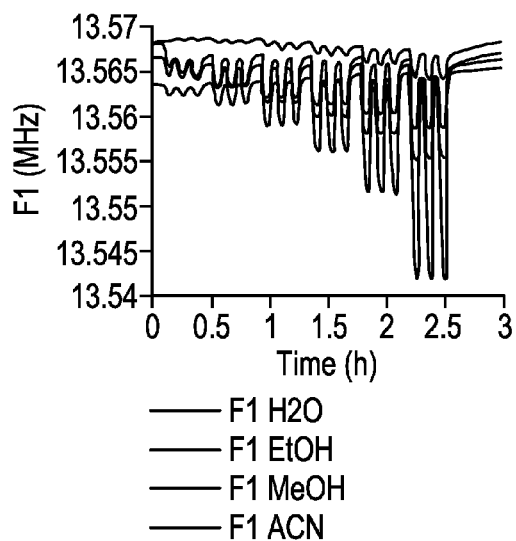
FIGS. 10A, 10B, 10C and 10D are graphical representations of examples of changes of measured parameters associated with FIG. 4 in accordance with the invention.
Figure 10B:
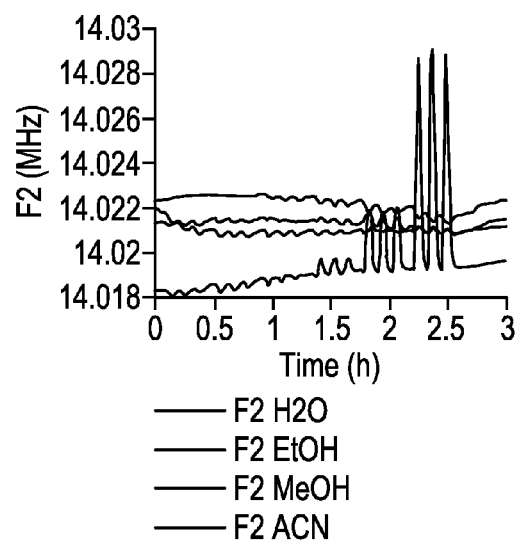
Figure 10C:
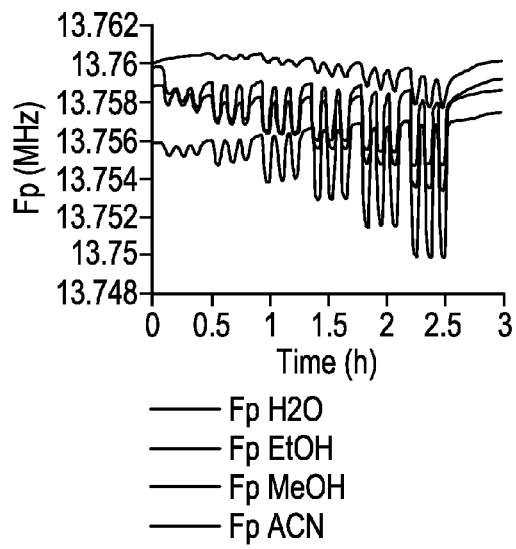
Figure 10D:
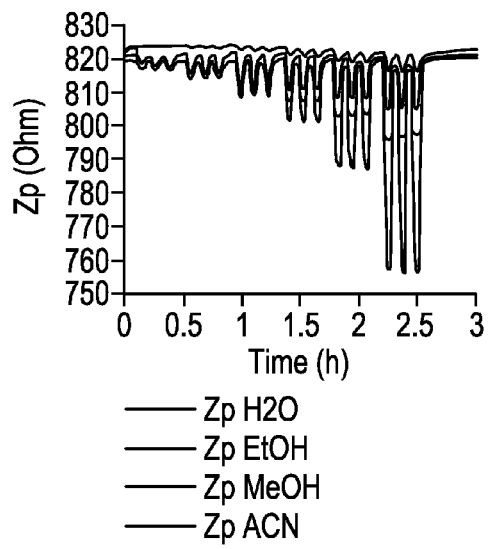
Figure 11A:
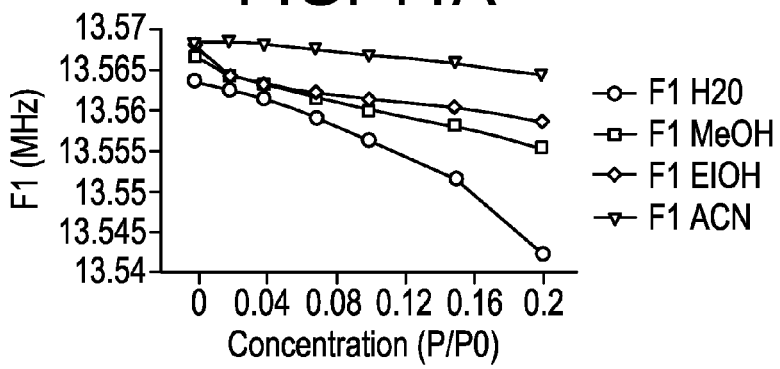
FIGS. 11A, 11B, 11C and 11D are graphical representations of examples of calibration curves of measured parameters associated with FIG. 4 in accordance with the invention.
Figure 11B:
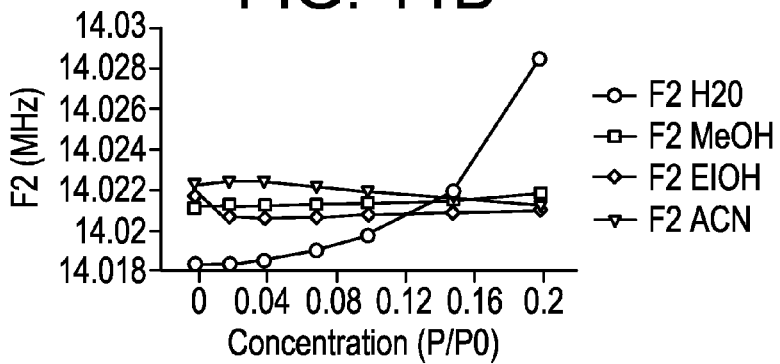
Figure 11C:
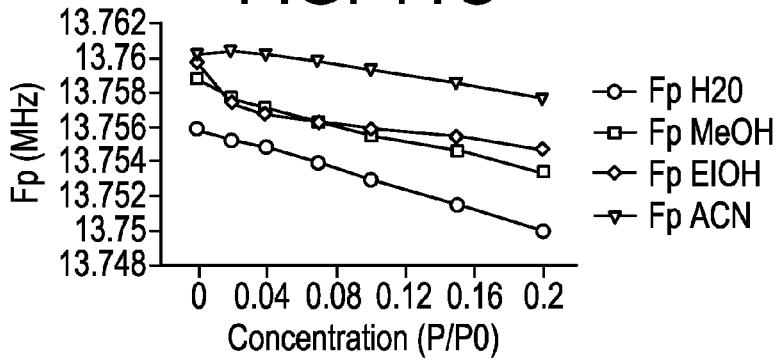
Figure 11D:
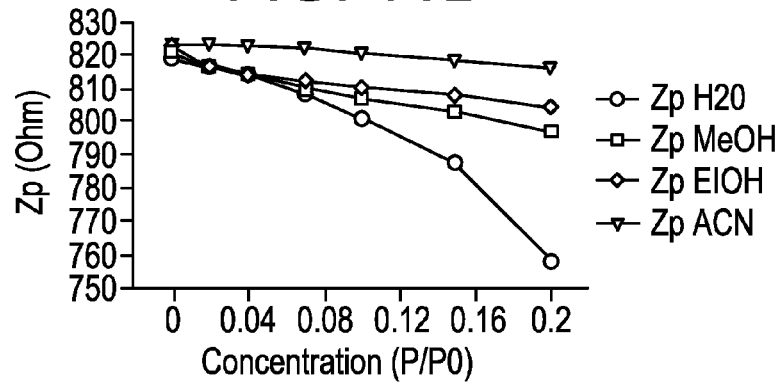
Figure 12:
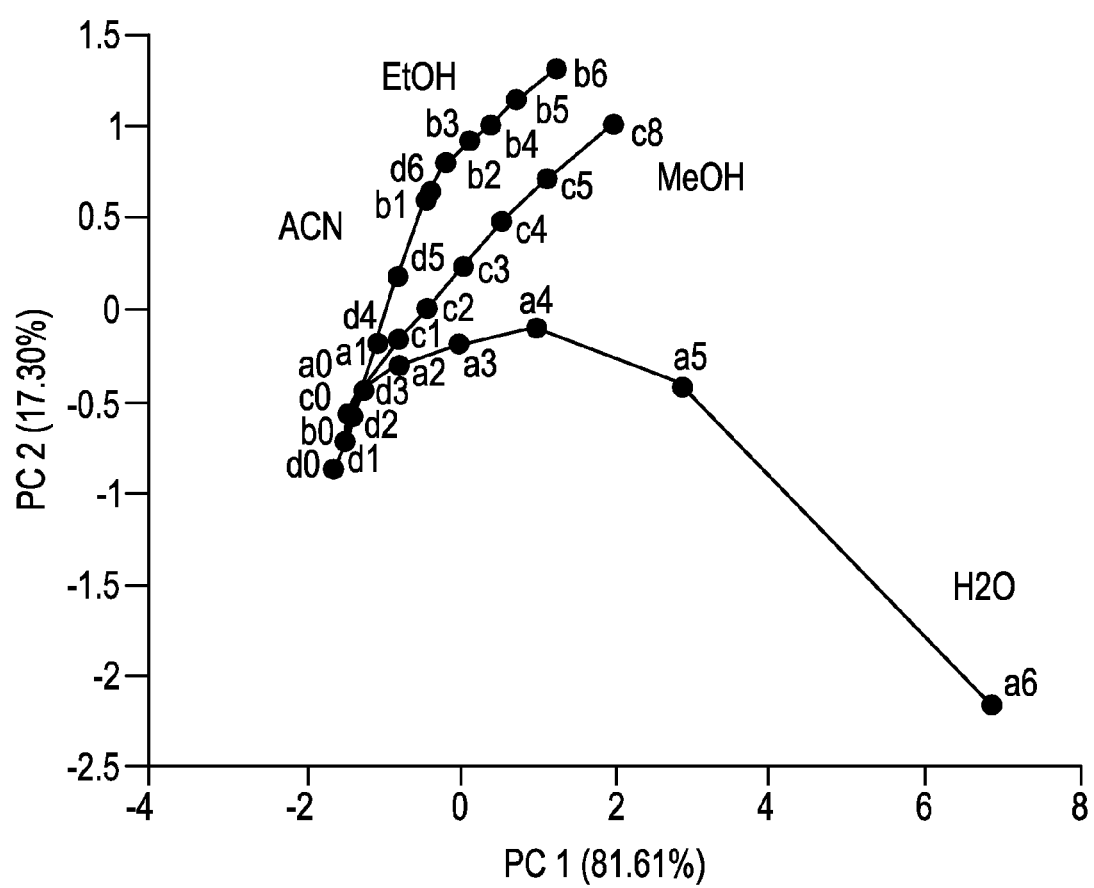
FIG. 12 is a graphical representation of an example of multivariate analysis of measure parameters associated with FIG. 4 in accordance with the invention.

At block 403, at the impedance analyzer 107 (FIG. 1) predetermined parameters and parameter changes of the measured complex impedance z are calculated from the plurality of RFID sensors in the array 103. Examples of these parameters include frequency and frequency shift of the maximum of the imaginary part of the complex impedance F1, frequency and frequency shift of the minimum of the imaginary part of the complex impedance F2, frequency and frequency shift of the maximum of the real part of the complex impedance Fp, and magnitude of the real part of the complex impedance is $Z_p$ as shown in FIG. 7. Equivalent electrical circuit parameters of the resonant circuit (FIGS. 2A-2D) are calculated by the impedance analyzer 107 or computer 109. There were experimental results performed to illustrate the utilization of all the components in FIG. 1 as illustrated in FIGS. 8 and 9. For FIG. 8, when 50 micro liters of 1M NaCL is added into 100 mL of water in the container 101, the RFID sensor 103 signal changed as shown. For FIG. 9, the kinetics of the RFID sensor 103 response was provided by the diffusion of NaCl into water as illustrated.

Next, at block 405 the computer 109 or the impedance analyzer 107 with the pattern recognition subcomponent applies univariate and multivariate analysis to the information or data collected from the plurality of RFID sensors in the array 103. Univariate analysis provides the capability to calculate a single parameter of interest. The multivariate analysis methods may include, for example, pattern recognition techniques, described above, such as principal components analysis (PCA), hierarchical cluster analysis (HCA), soft independent modeling of class analogies (SIMCA) and neural networks. Also, the multivariate analysis provides the capability for the improvement of quantification ability of the plurality of RFID sensors in the array 103 or sensor 103, outlier detection for robust identification, and single-parameter or multi-parameter analyte detection with a single sensor 103 (with examples of being temperature, pH, conductivity) where the parameters of interest are quantified at block 407.

In this instance, physical or chemical parameters are represented by temperature and pH while conductivity is represented by environmental parameters. For demonstration of multi-analyte measurements with a single RFID sensor 103 coated with a sensing film (Nafion polymer) 307, four analytes were tested at six concentrations each. These analytes included ethanol (EtOH), methanol (MeOH), acetonitrile (ACN), and water ($H_2O$) vapors, all at concentrations (partial pressures P) ranging from 0 to 0.2 of the saturated vapor pressure ($P_o$) which are described in FIGS. 9-12. Exact concentrations were 0, 0.02, 0.04, 0.07, 0.10, 0.15, and 0.20 $P/P_o$. Similarly, measurements of different pure liquids or liquid mixtures, and physical parameters can be done by those skilled in the art.

FIG. 9 demonstrates the measured response of Zp for four analytes ($H_2O$, EtOH, MeOH, and ACN) for six concentrations each. As shown in FIG. 9, measurements of a single parameter of the RFID sensor 103, for example Zp, cannot discriminate between different analytes. For example, if a signal Zp is changed from about 820 to about 805 Ohm, this change can be due to 0.1 $P/P_o$ of $H_2O$ or 0.15 $P/P_o$ of MeOH or 0.2 $P/P_o$ of EtOH. Thus, a single-parameter measurement of the RFID sensor 103 cannot discriminate between different analytes and their concentrations.

FIGS. 10A, 10B, 10C and 10D respectively demonstrate the dynamic changes of all measured parameters F1, F2, Fp, and Zp upon exposure of the RFID sensor 103 to four analytes ($H_2O$, EtOH, MeOH, and ACN) for six concentrations each. Clearly, measurements of multiple parameters provide additional means for selective determinations of more than one analyte with a single RFID sensor 103. For example, for FIG. 10B F2 response to $H_2O$ showed initially a decrease in signal upon exposure to small concentrations of $H_2O$. However, the response was switched upon expose to larger concentrations of $H_2O$, Such behavior was due to the combined effects of the nature of the sensor film (Nafion) and measured analyte ($H_2O$). However, when another, more nonpolar analyte was measured (such as ACN), the F2 response was always decreasing with exposure to as ACN.

FIGS. 11A, 11B, 11C and 11D respectively demonstrate the calibration curves at all measured parameters F1, F2, Fp, and Zp upon exposure of the RFID sensor 103 to four analytes ($H_2O$, EtOH, MeOH, and ACN) for six concentrations each. Depending on the measured parameter and analyte, the responses are linear or nonlinear, decreasing or increasing, or even have a more complex behavior. This richness of the information, its complexity, diversity, and its non-correlating nature, provides the capability for selective determination of analytes with a single RFID sensor 103. Results of the multivariate analysis of multi-parameter response of the RFID sensor 103 to the changes in $H_2O$, EtOH, MeOH, and ACN for six analyte concentrations each are presented in FIG. 12. These results were obtained by analyzing the measured parameters F1, F2, Fp, and Zp using principal components analysis methodology using Matlab with PLS Toolbox software.

Referring to FIG. 4, at block 407, the detected data from the multivariate analysis is transmitted from the measurement device 111 or impedance analyzer 107 to the computer 109, where the computer 109 will display at block 409 the data of interest from a given sensor or sensors of the plurality of RFID sensors in the array 103. The data display is in the form of a quantified measured environmental parameter of interest such as temperature, pH, conductivity and other parameters described above. The given range of frequencies from the antenna 301 is transmitted from the impedance analyzer to the computer 109. The display is in the form of a suitable screen or an electrical signal. At this point the user can decide if the process should end or if the data should be transmitted to an appropriate control device. If the user chooses not to deliver the data to the control device, then this process ends. At block 411, the control device acts upon or reacts on receiving a quantified value of a signal from the impedance analyzer 107, for example, to cool or warm up the container 101 upon receiving a temperature reading from the plurality of RFID sensors in the array 103 then the process ends. The control device may be an electrically driven fluid switch, valve, pump, healer, cooler or the like.

Figure 5:
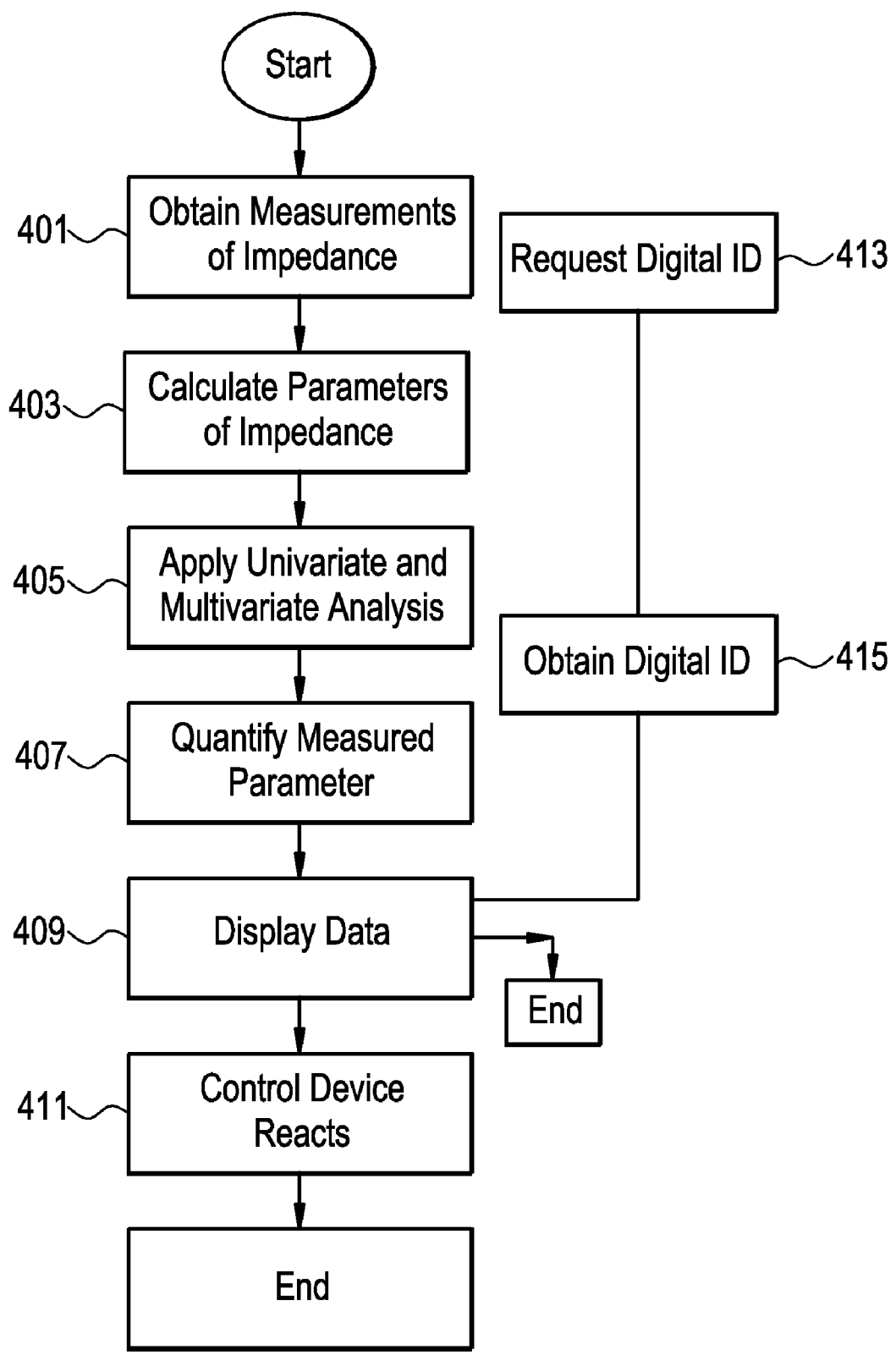
FIG. 5 depicts another flow chart of how a system for monitoring parameters in a solution is employed in accordance with the invention.
Figure 6:
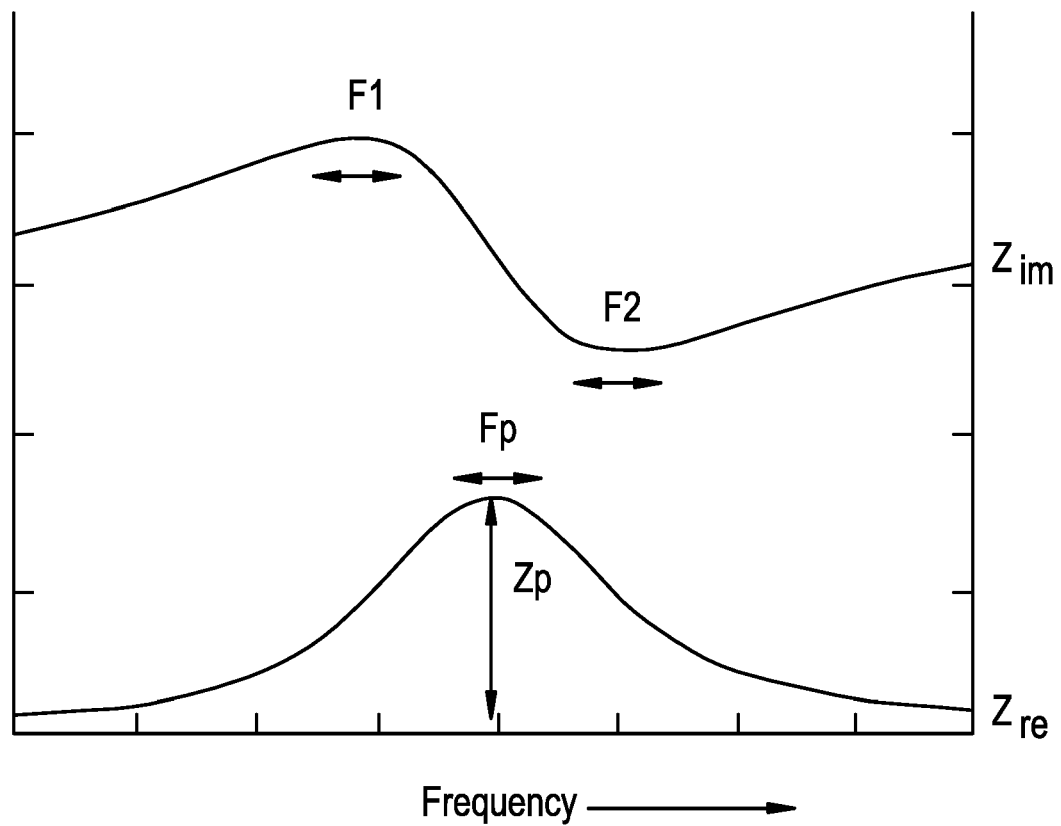
FIG. 6 is a graphical representation of an example of the utilization of the system for monitoring parameters in the solution of FIG. 1 in accordance with the invention.

FIG. 5 is a flow chart that shows another way of how the system for monitoring parameters in a solution is employed. This flow chart includes all of the components of FIG. 4 so these components will not be described herein. Additionally, this FIG. 5 includes, block 413 that is the RFID tag 102 with a sensor film 307 over the antenna that makes it a sensor 103 or without the sensor film 307 over the antenna 301, where the RFID reader 105 (measurement device 111) requests a digital id from the chip 303 off the RFID tag 102 and may obtain analyte data or parameter data if the antenna 301 is covered with a sensing film 307. At block 415, the RFID reader 105 (measurement device) obtains the digital ID transmitted to it by the RFID tag 102 and the analyte data or parameter data from the antenna 301 with sensing film 307. At block 409, the RFID reader 105 transmits the digital ID and analyte data or parameters to the computer 109 then this process operates in the same manner as FIG. 4. For FIGS. 4 and 5 the sensor 103 can be a single sensor or a sensor array.

Sensor coating is selected for proper chemical or biological recognition. Sensor transduction principle is selected to match the mechanism of response of the coating to the species of interest. For deposition of chemical or biological sensitive materials into RFID sensor 103, ink jet printing, screen printing, chemical and physical vapor deposition, spraying, draw coating, wet solvent coating, roll-to-roll coating (slot die, gravure coating, roll coating, dip coating etc), heat lamination and other deposition methods are used. To prevent the components of the sensor coatings from leaching into the environment of the container, known techniques are applied such as ion pairing, covalent bonding, and others. Optionally, an additionally dense, microporous, or mesoporous coating layer, such as expanded PTFE (e-PTFE), nanofiltration, and ultra filtration membranes can be used as a protective layer or permeselective layer to reduce bio-fouling, concentrate the specie(s) to be detected.

In one embodiment, the biological container 101 is preferably made from but not limited to the following materials, alone or in any combination as a multi-layer film: ethylene vinyl acetate (EVA) low or very low-density polyethylene (LDPE or VLDPE) ethyl-vinyl-alcohol (EVOH) polypropylene (PP), all of which are well known in the art. RFID tags typically comprise front antennas and microchips with a plastic backing (e.g., polyester, polyimide etc).

For combining the RFID sensor array 103 with the multilayer plastic films/sheet, the ultrasonic lamination, thermal lamination, hot-melt lamination are employed. In ultrasonic lamination process, at least a portion of a multilayer plastic film/sheet web (first sheet) used for making disposable bag is impinged with ultrasonic waves; the backside of the RFID tag (second sheet) with appropriate sensing materials coated on front antennas side are bonded onto the multilayer plastic film/sheet. Optionally, corona, plasma, and flame treatment of the plastic film/sheet is performed before the lamination process. In another embodiment, adhesives, such as a pressure sensitive adhesive, moisture cure, and radiant cure adhesives can be used to bond the RIFD tag 102 to the biological container 101.

This invention provides a system that allows a user to simply determine what kind of solution is in a container and the concentrations and levels of chemical, physical and biological parameters of interest. The container includes a radio frequency identification (RFID) sensor with a sensor film that enables the sensor to effectively determine the material in the solution.

It is intended that the foregoing detailed description of the invention be regarded as illustrative rather than limiting and that it be understood that it is the following claims, including all equivalents, which are intended to define the scope of the invention.

What is claimed is:

1. A system for measuring multiple parameters comprising:
   a container having a solution, at least one sensor in conjunction with a tag is in proximity to an impedance analyzer and a reader that constitute a measurement device;
   wherein the at least one sensor is configured to determine at least two parameters of the solution;
   the tag is configured to provide a digital ID associated with the at least one sensor, wherein the container is in proximity to the reader and an impedance analyzer; and
   wherein the impedance analyzer is configured to receive a given range of frequencies from the at least one sensor based on the at least two parameters and calculate changes of the at least two parameters by using multivariate analyses on the real and imaginary parts of the complex impedance measured by the impedance analyzer as a function of the received frequencies.

2. The system of claim 1, wherein the container is connected to a computer.

3. The system of claim 2, wherein the measurement device is configured to read the at least two parameters from the at least one sensor.

4. The system of claim 3, wherein the computer is configured to display the at least two parameters from the at least one sensor.

5. The system of claim 1, wherein the container is a disposable container.

6. The system of claim 1, wherein the container is a plastic container.

7. The system of claim 1, wherein the solution is selected from the group consisting of fluid, blood and gas.

8. The system of claim 7, wherein the solution is blood that comprises the following materials: creatineine, urea, lactate dehydroensea and alkaline potassium.

9. The system of claim 7, wherein the solution is gas or dissolved gas that comprises $CO_2$, $O_2$, NOx.

10. The system of claim 7, wherein the solution includes a toxic industrial agent comprising Ammonia, Acetone cyanohydrin.

11. The system of claim 7, wherein the solution contains prokaryotic cells.

12. The system of claim 7, wherein the solution contains eukaryotic cells.

13. The system of claim 7, wherein the solution is gas that comprises $CO_2$ and $O_2$.

14. The system of claim 7, wherein the solution is dissolved gas that comprises $CO_2$ and $O_2$.

15. The system of claim 1, wherein the reader is a radio frequency identification (RFID) reader.

16. The system of claim 1, wherein the at least one sensor is a plurality of sensors in an array.

17. The system of claim 1, wherein the plurality of sensors in the array are a plurality of RFID sensors in an array.

18. The system of claim 1, wherein the at least two parameters are comprised of a conductivity measurement, a pH level, a temperature, a blood relevant measurement, a biological measurement, an ionic measurement, a non-ionic measurement and a non-conductivity measurement.

19. The system of claim 1, wherein the at least one sensor is covered in a sensor film, wherein the sensor film determines the at least two parameters of the solution.

20. The system of claim 19, wherein the sensor film is selected from the group consisting of a polymer film, an organic film, an inorganic film, a biological composite film and a nano-composite film.

21. The system of claim 19, wherein the sensor film is selected from the group consisting of a hydrogel film, a sol-gel film, a carbon black-polymer film, a carbon nanotube-polymer film, a metal nanoparticle-polymer film and an electrospun nanofibers, film.

22. The system of claim 1, wherein the container is made of a polymeric material.

23. The system of claim 22, wherein the container is made of a pre-sterilized polymeric material.

24. The system of claim 1, wherein the solution includes a biological material from the group comprising a bacteria, a recombinant protein, a virus, a vaccine or living tissue.

25. A system for measuring multiple parameters comprising:
   a container having a solution and at least one sensor;
   a measurement device in communication with the at least one sensor;
   wherein the at least one sensor is configured to determine at least two parameters of the solution;
   the measurement device is configured to receive the at least two parameters from the at least one sensor;
   wherein the container is in proximity to the measurement device; and
   the measurement device is configured to receive a given range of frequencies from the at least one sensor based on the at least two parameters to measure complex impedance and calculate parameter changes by using multivariate analyses on the real and imaginary parts of the complex impedance.

26. A system for measuring multiple parameters comprising:
   a container having a solution and at least one sensor with a digital ID tag;
   a measurement device in communication with the sensor with the tag;
   wherein the at least one sensor is configured to determine at least two parameters of the solution;
   the measurement device is configured to receive the at least two parameters from the at least one sensor and digital ID from the tag;
   wherein the container is in proximity to measurement device; and
   the measurement device is configured to receive a given range of frequencies from the at least one sensor based on the at least two parameters to measure complex impedance and calculate parameter changes by using multivariate analyses on the real and imaginary parts of the complex impedance.

27. The system of claim 26, wherein the at least one sensor is passive.

28. The system of claim 26, wherein the at least one sensor is semi active.

29. The system of claim 26, wherein the at least one sensor is active.

30. A system for measuring multiple parameters comprising:
- a container having a solution and at least one sensor;
- a measurement device in communication with the at least one sensor;
- wherein the at least one sensor is configured to determine at least two parameters of the solution;
- the measurement device is configured to receive the at least two parameters from the at least one sensor;
- wherein the container is in proximity to the measurement device;
- the measurement device is configured to receive a given range of frequencies from the at least one sensor based on the at least two parameters to measure complex impedance and calculate parameter changes by using multivariate analyses on the real and imaginary parts of the complex impedance; and
- the measurement device sends a predetermined signal to a control device.

* * * * *